(12) United States Patent
Roy

(10) Patent No.: US 10,898,547 B2
(45) Date of Patent: Jan. 26, 2021

(54) METHOD OF TREATMENT OF BREAST OR COLON CANCER BY ADMINISTERING MUSCLE STIMULATED MYOKINES

(71) Applicant: Unicorn Therapeutics, LLC, Evanston, IL (US)

(72) Inventor: Hemant Kumar Roy, Chestnut Hill, MA (US)

(73) Assignee: Unicorn Therapeutics, LLC, Evanston, IL (US)

( * ) Notice: Subject to any disclaimer, the term of this patent is extended or adjusted under 35 U.S.C. 154(b) by 0 days.

(21) Appl. No.: 16/300,472

(22) PCT Filed: May 10, 2017

(86) PCT No.: PCT/US2017/031975
§ 371 (c)(1),
(2) Date: Nov. 9, 2018

(87) PCT Pub. No.: WO2017/196989
PCT Pub. Date: Nov. 16, 2017

(65) Prior Publication Data
US 2019/0142900 A1   May 16, 2019

Related U.S. Application Data

(60) Provisional application No. 62/334,070, filed on May 10, 2016.

(51) Int. Cl.
| | | |
|---|---|---|
| *A61K 38/19* | (2006.01) | |
| *G01N 33/68* | (2006.01) | |
| *A61K 45/06* | (2006.01) | |
| *A61K 38/09* | (2006.01) | |
| *A61P 35/00* | (2006.01) | |
| *A61K 35/34* | (2015.01) | |
| *C12N 5/077* | (2010.01) | |
| *A61K 31/5377* | (2006.01) | |
| *A61K 31/69* | (2006.01) | |
| *A61K 38/15* | (2006.01) | |
| *A61K 31/7048* | (2006.01) | |
| *A61K 31/704* | (2006.01) | |
| *A61K 31/58* | (2006.01) | |
| *A61K 31/517* | (2006.01) | |
| *A61K 31/4184* | (2006.01) | |
| *A61K 31/506* | (2006.01) | |
| *C12N 5/09* | (2010.01) | |
| *A61K 33/24* | (2019.01) | |
| *A61K 31/337* | (2006.01) | |
| *A61K 31/513* | (2006.01) | |
| *A61K 38/17* | (2006.01) | |
| *B01L 3/00* | (2006.01) | |

(52) U.S. Cl.
CPC ............ *A61K 38/19* (2013.01); *A61K 31/337* (2013.01); *A61K 31/4184* (2013.01); *A61K 31/506* (2013.01); *A61K 31/513* (2013.01); *A61K 31/517* (2013.01); *A61K 31/5377* (2013.01); *A61K 31/58* (2013.01); *A61K 31/69* (2013.01); *A61K 31/704* (2013.01); *A61K 31/7048* (2013.01); *A61K 33/24* (2013.01); *A61K 35/34* (2013.01); *A61K 38/09* (2013.01); *A61K 38/15* (2013.01); *A61K 38/1709* (2013.01); *A61K 45/06* (2013.01); *A61P 35/00* (2018.01); *B01L 3/5085* (2013.01); *C12N 5/0658* (2013.01); *C12N 5/0693* (2013.01); *G01N 33/6863* (2013.01); *B01L 2300/025* (2013.01); *C12N 2502/1335* (2013.01)

(58) Field of Classification Search
None
See application file for complete search history.

(56) References Cited

U.S. PATENT DOCUMENTS

2010/0104660 A1    4/2010  Yu

FOREIGN PATENT DOCUMENTS

WO    2014150772 A1    9/2014

OTHER PUBLICATIONS

Bostrom et al. A PGC1 alpha-dependent myokine that drives browning of white fat and thermogenesis. Nature, 481, 463-469. 2012. (Year: 2012).*
Gannon et al.—Effects of the exercise-inducible myokine irisin on malignant and non-malignant breast epithelial cell behavior in vitro . Int. J. Cancer: 136, E197-E202, 2015. (Year: 2015).*
Hojman et al.—Exercise-induced muscle-derived cytokines inhibit mammary cancer cell growth. Am. J Physiol Endocrinol Metab 301: E504-E510, 2011. (Year: 2011).*
Zips et al. —New anticancer agents: In vitro and in vivo evaluation. In Vivo, 19, 1-8, 2005. (Year: 2005).*
List of cancer-types—Wikipedia (https://en.wikipedia.org/wiki/List_of_cancer_types—accessed May 22, 2020). (Year: 2020).*
Types of Cancer—NCI (https://www.cancer.gov/about-cancer/understanding/what-is-cancer;—accessed May 22, 2020). (Year: 2020).*
Coleman et al.,Discerning clinical responses in breast cancer based on molecular signatures, Am. J. Pathol., 187, 2199-2207, 2017. (Year: 2017).*
Han et al., FOXC1: an emerging marker and therapeutic target for cancer. Oncogene 36, 3957-3963, 2017. (Year: 2017).*
Geyer et al. The spectrum of triplenegative breast disease. Am J Pathol 187: 2139-2151, 2017. (Year: 2017).*
Glazer et al., PPARs as determinants of the estrogen receptor lineage: use of synthetic lethality for the treatment of estrogen receptor negative breast cancer. Oncotarget, 8, 50337-50341, 2017. (Year: 2017).*
Wu et al., Nanomedicine applications in the treatment of breast cancer: current state of the art. Int. J. Nanomed. 12, 5879-5892, 2017. (Year: 2017).*

(Continued)

*Primary Examiner* — Elly-Gerald Stoica
(74) *Attorney, Agent, or Firm* — Perkins Coie LLP

(57) ABSTRACT

The present disclosure provides methods for generating myokines in vitro and compositions comprising myokines. Such compositions may be used for treatment of diseases such as cancer and fatty liver disease.

13 Claims, 18 Drawing Sheets

(56) References Cited

OTHER PUBLICATIONS

Wang et al., Dysregulation of long non-coding RNA in breast cancer: an overview of mechanism and clinical implication. Oncotarget, 8, 5508-5522, 2017. (Year: 2017).*

Tafazoli A., Coenzyme Q10 in breast cancer care. Future Oncol. 13, 1035-1041, 2017. (Year: 2017).*

Gonzalez et al., 2017 update on the relationship between diabetes and colorectal cancer: epidemiology, potential molecular mechanisms and therapeutic implications. Oncotarget, 8, 18456-18485, 2017. (Year: 2017).*

Jones et al., Specific mutations in KRAS codon 12 are associated with worse overall survival in patients with advanced and recurrent colorectal cancer. British J. Cancer 116, 923-929, 2017. (Year: 2017).*

Goblirsch et al. MicroRNAs as a tool to aid stratification of colorectal cancer patients and to guide therapy. Pharmacogenomics 18, 1027-1038, 2017. (Year: 2017).*

Geng et al., Molecular targeted drugs and treatment of colorectal cancer: recent progress and future perspectives. Ca. Biother. Radiopharm., 32, 149-160, 2017. (Year: 2017).*

Kavousipour et al., Novel biotechnology approaches in colorectal cancer diagnosis and therapy. Biotechnol. Lett. 39, 785-803, 2017. (Year: 2017).*

Biljsma et al., Molecular subtypes in cancers of the gastrointestinal tract. Nature reviews | gastroenterology & hepatology, 14 333-342, 2017. (Year: 2017).*

Nowacka-Zawisza et al., DNA methylation and histone modifications as epigenetic regulation in prostate cancer. Oncol. Reports, 38, 2587-2596, 2017. (Year: 2017).*

Diab et al., Targeted therapy in ovarian cancer. A comprehensive systematic review of literature. Anticancer Res. 37, 2809-2815, 2017. (Year: 2017).*

Kroeger et al., Pathogenesis and heterogeneity of ovarian cancer. Curr Opin Obstet Gynecol 29, 26-34, 2017. (Year: 2017).*

Gupta et al., Molecular genetics complexity impeding research progress in breast and ovarian cancers (Review). Mol. Clin. Oncol., 7, 3-14, 2017. (Year: 2017).*

Lee et al., Treatment strategies for endometrial cancer: current practice and perspective. Curr Opin Obstet Gynecol. 29, 47-58, 2017. (Year: 2017).*

Wilczynski et al., An update of the classical Bokhman's dualistic model of endometrial cancer. Menopause Rev. 15, 63-68, 2017. (Year: 2017).*

Jeske et al., FGFR2 mutations are associated with poor outcomes in endometrioid endometrial cancer: An NRG Oncology/Gynecologic Oncology Group study. Gynecologic Oncology 145, 366-373, 2017. (Year: 2017).*

Bernstein et al., Endometrial cancer evolution: new molecular-biologic types and hormonal-metabolic shifts. Future Oncol. 13, 2593-2605, 2017. (Year: 2017).*

Han et al., Sample types applied for molecular diagnosis of therapeutic management of advanced non-small cell lung cancer in the precision medicine. Clin Chem Lab Med 55, 1817-1833, 2017. (Year: 2017).*

Weeber et al., Tumor organoids as a pre-clinical cancer model for drug discovery, Cell Chem. Biol. 24, 1092-1100, 2017. (Year: 2017).*

Delacruz , et al., "Towards identification of factors in exercise-induced colorectal cancer prevention: development of a novel cell culture model, Su2057", Delacruz et al., Towards identification of factors in exercise-induced colorectal cancer prevention: development of a novel cell culture model, Su2057; Gastroenterology, Apr. 1, 2016, vol. 150, No. 4, p. S623.

* cited by examiner

| MILLIPLEX Mouse Myokine Analyst Detail Report |||||
|---|---|---|---|---|---|
| Analyte | IL-10 | LIF | IL-6 | TNF-alpha | IL-15 |
| Sample | pg/ml | pg/ml | pg/ml | pg/ml | pg/ml |
| Unstimulated 1 | 1.78 | 279.9 | 747.06 | 6.01 | 3.33 |
| Unstimulated 2 | <0.81↓ | 176.67 | 412.51 | 2.88 | 2.04 |
| Unstimulated 3 | 1.18 | 184.37 | 446.62 | 3.42 | 2.04 |
| Unstimulated 4 | <0.81↓ | 127.79 | 292.62 | 2.35 | <1.73↓ |
| Stimulated 1 | 11.43 | 844.58 | >34024↑ | 25.26 | 10.53 |
| Stimulated 2 | 9.92 | 763.47 | >34024↑ | 22 | 9.33 |
| Stimulated 3 | 9.92 | 613.17 | 29187↑ | 17.08 | 7.04 |

| Standard Curve: ||||||
|---|---|---|---|---|---|
| Analyte | Chi | $R^2$ | CV | MinDC | MaxDC |
| IL-10 | 0.090% | 0.999 | 2.58% | 0.81 | 8634 |
| LIF | 0.085% | 0.999 | 2.61% | 1.27 | 13387 |
| IL-6 | 0.087% | 0.999 | 2.81% | 3 | 34024 |
| TNF-alpha | 0.085% | 0.999 | 2.48% | 2.23 | 6657 |
| IL-15 | 0.095% | 0.999 | 2.72% | 1.73 | 7181 |

*FIG. 12*

METHOD OF TREATMENT OF BREAST OR COLON CANCER BY ADMINISTERING MUSCLE STIMULATED MYOKINES

PRIORITY DATA

This application is a U.S. 371 National Stage Application of International PCT Application No. PCT/US2017/031975 filed on May 10, 2017, which claims priority to U.S. Provisional Patent Application No. 62/334,070, filed on May 10, 2016, the entire contents of each of which are incorporated herein by reference and relied upon.

BACKGROUND

Physical activity has numerous beneficial health effects and is an important health behavior for the prevention and management of a myriad of human diseases. In particular, exercise has been shown to reduce the risk of developing some cancers, help cancer survivors cope with and recover from treatments, improve the long-term health of cancer survivors, and even reduce the risk of recurrence in some groups. However, the mechanism of action remains unknown.

SUMMARY

This disclosure is predicated on the discovery that in vitro cultures of cells can be stimulated to secrete factors that can be used for the treatment and/or prevention of disease, for example, cancer.

In some aspects, this disclosure provides in vitro methods for generating myokines comprising: exposing myotubules in a culture medium to electrical pulse stimulation (FPS) conditions for a period of time to generate stimulated muscle medium; and separating the stimulated muscle medium from at least a portion of the myotubules.

In other aspects, this disclosure provides compositions comprising an amount of stimulated muscle medium and/or myokines isolated therefrom and a pharmaceutical excipient.

In other aspects, this disclosure provides methods of treating and/or preventing a cancer or a metabolic disease in a patient in need thereof comprising administering to the patient an effective amount of a composition comprising stimulated muscle medium and/or myokines isolated therefrom.

In yet another aspect, this disclosure provides methods for titrating physical activity for the treatment and/or prevention of cancer, which methods comprise: detecting or measuring the level of a myokine in a biological sample isolated from a subject; and reporting the level of the myokine to the subject or providing to the subject instruction to or not to exercise, wherein the instruction is determined from the level of myokine detected or measured.

In still another aspect, this disclosure provides devices for titrating physical activity for the treatment and/or prevention of cancer, which devices comprise: an assembly configured to receive a biological sample; a detector for measuring an amount of myokine in biological sample; and a display for reporting the amount of myokine in the biological sample or an instruction to or not to exercise.

In some embodiments, the methods further comprise fractionating and/or concentrating the stimulated muscle medium to enrich for or isolate a specific myokine or combination of myokine s.

In some embodiments, the FPS conditions are generated by a C-Pace Cell Culture FP Stimulator.

In some embodiments, the EPS conditions comprise an electrical potential of between about 15 V to about 50 V.

In some embodiments, the period of time to generate stimulated muscle medium is from about 6 hours to about 24 hours. In other embodiments, the period of time to generate stimulated muscle medium is from about 9 hours to about 12 hours.

In some embodiments, the amount of stimulated muscle medium and/or myokines is a therapeutically effective amount.

In some embodiments, the compositions comprise a preservative, a cryopreservative, a carrier protein, or combinations thereof.

In some embodiments, the composition is formulated for intravenous, intraperitoneal, or intratumoral delivery. In other embodiments, the composition is present in a skin patch.

In some embodiments, the cancer is selected from the group consisting of breast cancer, colorectal cancer, endometrial cancer, hepatocellular carcinoma, non-small cell lung cancer, ovarian cancer, and prostate cancer.

In some embodiments, the cancer is a solid tumor. In some embodiments, the solid tumor is reduced in size.

In some embodiments, the composition is administered by direct injection or perfusion into the solid tumor. In other embodiments, the composition is administered intravenously, intraperitoneally, intratumorally, subcutaneously, or orally.

In some embodiments, the metabolic disease is a fatty liver disease, dyslipidemia, metabolic syndrome, a cardiovascular disease, obesity, a leptin disorder, or any combination thereof. In some embodiments, the fatty liver disease is hepatic steatosis, non-alcoholic steatohepatitis, non-alcoholic fatty liver disease (NAFLD), elevated liver cholesterol level, elevated liver triglyceride level, elevated liver fatty acid level, elevated liver LDL-cholesterol level, elevated liver VLDL cholesterol level, or elevated liver non-HDL cholesterol level, or any combination thereof.

In some embodiments, the treating results in slowed progression and/or amelioration of the cancer and/or metabolic disease as compared to a patient or population of patients treated with a placebo or another agent that is not stimulated muscle medium and/or myokines isolated therefrom.

In some embodiments, the methods comprise administering to the patient a second therapeutic that is different than said stimulated muscle medium and/or myokines isolated therefrom, for example, the second therapeutic is selected from the group consisting of abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, imatinib, hydroxyurea, imatinib, lapatinib, leuprorelin, melphalan, methotrexate, mitoxantrone, nedaplatin, nilotinib, oxaliplatin, paclitaxel, pazopanib, pemetrexed, picoplatin, romidepsin, satraplatin, sorafenib, vemurafenib, sunitinib, teniposide, triplatin, vinblastine, vinorelbine, vincristine, and cyclophosphamide.

In some embodiments, a sub-therapeutic dose of the second therapeutic is administered.

In some embodiments, the stimulated muscle medium and/or myokines and the second therapeutic are delivered substantially simultaneously, concurrently or sequentially.

In some embodiments, the stimulated muscle medium and/or myokines comprise TNF-α, IL-6, IP-10/CXCL10/

CRG2, RANTES/CCL5, GM-CSF, I-309/CCL1/TCA-3, Serpin A8/Angiotensin II, or any combination thereof.

In some embodiments, the stimulated muscle medium and/or myokines comprise no or substantially no cathepsin L (CTSL, CTSL1), pentraxin-3/TSG-14 (PTX3), adiponectin/Acrp30 (ADIPOQ), vascular endothelial growth factor (VEGF), angiopoietin-1 (ANGPT1), IGFBP-3, IGFBP-4, MIF, IGFBP-rp1/IGFBP-7, Serpin A12/Vaspin, TMP-1, KC/CXCL1, JE/CCL2/MCP-1, M-CSF, TNF-α or any combination thereof.

In some embodiments, the subject increases an amount, intensity or a duration of an exercise when the level of myokine is below a pre-determined baseline.

In some embodiments, the device is wearable or handheld. In other embodiments, the device is configured to communicate with a wearable or handheld device.

DESCRIPTION OF THE DRAWINGS

The foregoing summary, as well as the following detailed description of the disclosure, will be better understood when read in conjunction with the appended figures. It should be understood that the disclosure is not limited to the precise arrangements, examples, and instrumentalities shown.

FIG. 12 shows results of a myokine myoplex assay to detect level of cytokines present in a sample following 8 hours stimulation ("Stimulated 1", "Stimulated 2", "Stimulated 3") or control, no stimulation ("Unstimulated 1", "Unstimulated 2", "Unstimulated 3", "Unstimulated 4").

DETAILED DESCRIPTION

Figure 1:
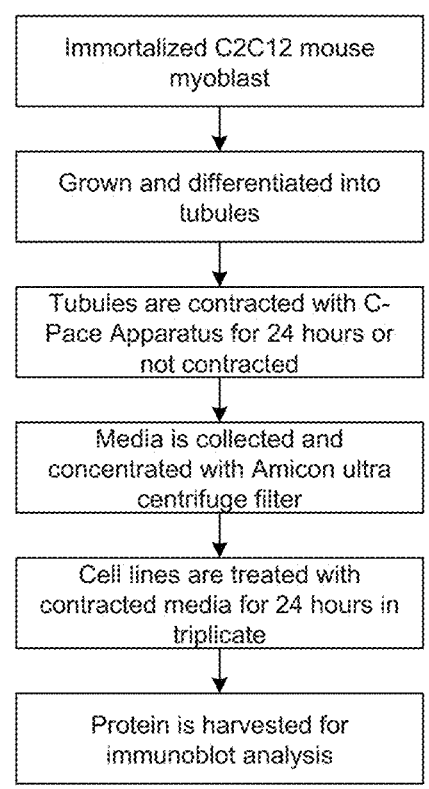
FIG. 1 is a high level schematic of the primary steps performed in one embodiment of the present disclosure.

It is to be understood that this disclosure is not limited to particular embodiments described, as such may, of course, vary. It is also to be understood that the terminology used herein is for the purpose of describing particular embodiments only, and is not intended to be limiting, since the scope of this disclosure will be limited only by the appended claims.

The detailed description of the disclosure is divided into various sections only for the reader's convenience and disclosure found in any section may be combined with that in another section. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated by reference to disclose and describe the methods and/or materials in connection with which the publications are cited.

All numerical designations, e.g., pH, temperature, time, concentration, and molecular weight, including ranges, are approximations which are varied (+) or (−) by increments of 0.1 or 1.0, where appropriate. It is to be understood, although not always explicitly stated that all numerical designations are preceded by the term "about." It also is to be understood, although not always explicitly stated, that the reagents described herein are merely exemplary and that equivalents of such are known in the art.

It must be noted that as used herein and in the appended claims, the singular forms "a", "an", and "the" include plural referents unless the context clearly dictates otherwise. Thus, for example, reference to "a myokine" includes a plurality of myokines.

Definitions

The term "about" when used before a numerical designation, e.g., temperature, time, amount, concentration, and such other, including a range, indicates approximations which may vary by (+) or (−) 10%, 5% or 1%.

Also as used herein, "and/or" refers to and encompasses any and all possible combinations of one or more of the associated listed items, as well as the lack of combinations when interpreted in the alternative ("or").

"Comprising" or "comprises" is intended to mean that the compositions, for example cell culture media, and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

"Optional" or "optionally" means that the subsequently described event or circumstance can or cannot occur, and that the description includes instances where the event or circumstance occurs and instances where it does not.

As used herein the terms "basal media" and "basal medium," are used interchangeably, and refer a culture media without additives. Basal media can include a mixture of different basal media.

The term "concentrating" as used herein can refer to increasing the total solids (e.g., myokines) in the composition, such as by removing the liquid basal media and/or culture media to produce a concentrated composition.

The term "cryopreservative" generally includes agents which provide stability to the composition against freezing stresses, presumably by being preferentially excluded from the surface. They may also offer protection during long-term product storage. Examples are polymers such as dextran and polyethylene glycol; sugars such as sucrose, glucose, trehalose, and lactose; surfactants such as polysorbates; and amino acids such as glycine, arginine, and serine.

As used herein the terms "culture media" and "culture medium" are used interchangeably and refer to a solid or a liquid substance used to support the growth of cells (e.g., myotubules). Preferably, the culture media as used herein refers to a liquid substance capable of maintaining myotubules. The culture media can be a water-based media which includes a combination of ingredients such as salts, nutrients, minerals, vitamins, amino acids, nucleic acids, proteins such as cytokines, growth factors and hormones, all of which are needed for cell proliferation and are capable of maintaining stem cells in an undifferentiated state. For example, a culture media can be a synthetic basal media supplemented with the necessary additives. Preferably, all ingredients included in the culture media of the present disclosure are substantially pure and tissue culture grade.

An "effective amount" is an amount of a composition or component (e.g., stimulated muscle medium or myokines) sufficient to effect beneficial or desired results. An effective amount can be in one or more administrations, applications or dosages. Determination of these parameters is well within the skill of the art. These considerations, as well as effective formulations and administration procedures are well known in the art and are described in standard textbooks.

The term "electrical pulse stimulation" (EPS) refers to the use of an electric current to stimulate a cell, for example, to stimulate contraction of a muscle cell. Electrical impulses are generated by any device known to one of skill in the art and delivered through electrode probes in proximity to the cells to be stimulated. The impulses can mimic the action potential coming from the central nervous system that cause muscle cells to contract.

The term "fractionating" as used herein refers to the process of dividing the stimulated muscle medium into smaller sub-portions or fractions on the basis of some physical, chemical or biochemical property and using any technique known of one skilled in the art. Non-limiting examples of some fractionating techniques include, column chromatography; HPLC; FPLC; matrix-affinity chromatography; reverse-phase chromatography; and electrophoretic separation.

As used herein, the term "myokine" refers to peptides or polypeptides, bioactive lipids, second messengers, etc. derived from muscle cells. The term "muscle cells" refers to those cells making up contractile tissue of animals. Muscle cells are derived from the mesodermal layer of embryonic germ cells. Muscle cells contain contractile filaments that move past each other and change the size of the cell. They are classified as skeletal, cardiac, or smooth muscles.

The term "therapeutic" as used herein in reference to treatment of cancer means any therapeutically useful agent and/or procedure for the treatment, remission or attenuation of a disease state, physiological condition, symptoms, or etiological factors, or for the evaluation or diagnosis thereof. A therapeutic agent may be a chemotherapeutic agent, for example, mitotic inhibitors, topoisomerase inhibitors, steroids, anti-tumor antibiotics, antimetabolites, alkylating agents, enzymes, proteasome inhibitors, any combinations thereof, and the like.

The term "treating" or "treatment" covers the treatment of a disease or disorder (e.g., cancer), in a subject and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, "treating" or "treatment" refers to the killing of cancer cells. The term "kill" with respect to a cancer treatment is directed to include any type of manipulation that will lead to the death of that cancer cell or at least a portion of a population of cancer cells.

In vitro Production and Processing of Myokines

As will be apparent to the skilled artisan upon reading this disclosure, the present disclosure relates to methods of producing and processing myokines.

In some aspects provided herein are in vitro methods for generating myokines comprising: (a) exposing myotubules in a culture medium to electrical pulse stimulation (EPS) conditions for a period of time to generate stimulated muscle medium; and (b) separating the stimulated muscle medium from at least a portion of the myotubules.

The EPS conditions can be generated by any method and/or device known in the art to deliver electrical stimulation to cultivated cells in vitro. Non-limiting examples of commercially available devices useful for generating the FPS conditions are a C-Pace Cell Culture FP Stimulator (Ion Optix, Westwood, Mass., USA) and a Grass S-48 stimulator (Grass Instruments, Quincy, Mass., USA).

In some embodiments, the FPS conditions comprise an electrical potential of between about 15 V to about 50 V. In other embodiments, the period of time for exposing the myotubules to FPS conditions is from about 6 hours to about 24 hours, for example, from about 9 hours to about 12 hours. In other embodiments, the period of time for exposing the myotubules to FPS conditions is less than one hour, less than two hours, less than three hours, less than five hours, less than six hours, less than seven hours, less than eight hours, less than nine hours, less than ten hours less than eleven hours, less than twelve hours, less than fifteen hours, less than twenty hours, less than twenty-four hours, less than thirty-six hours, or less than forty-eight hours. In one preferred embodiment, the period of time for exposing the myotubules to FPS conditions is about nine hours.

Some FPS conditions useful for the present disclosure include those listed in Table 1.

TABLE 1

EPS Conditions

| EPS Conditions | (1) Exercise/myokine/ HCC project | (2) Protocol for exercise project | (3) Materials and Methods |
|---|---|---|---|
| Frequency (Hz) | 1 | 1 | 1 |
| Pulse duration (ms) | 3 | 2 | 3 |
| Intensity (V) | 50 | 40 | 20 |
| Duration of EPS (hrs) | 9 | 24 | 12 |
| Fractionation | 5-20 kDa collected, then concentrated using 3 kDa Amicon tube | Concentrate in 3 kDa MWCO | Concentrate in 3 kDa MWCO |

In some embodiments, the cells of the disclosure are cultured in conditions of 1-20% oxygen ($O_2$) and 5% carbon dioxide ($CO_2$). In some embodiments, the cells of the present disclosure are cultured under hypoxic conditions (e.g., in the presence of less than 10% $O_2$). In some embodiments, the cells of the present disclosure are cultured at about 37° C. In some embodiments, the cells of the present disclosure can be cultured at about 37° C., 5% $CO_2$ and 10-20% $O_2$.

In some aspects provided herein are methods for processing the muscle stimulated medium and/or myokines. In some embodiments, the methods comprise fractionating and/or concentrating the stimulated muscle medium to enrich for or isolate a specific myokine or combination of myokines. Non-limiting examples of some fractionating techniques include, column chromatography; HPLC; FPLC; matrix-affinity chromatography; reverse-phase chromatography; and electrophoretic separation. Non-limiting examples of techniques for concentrating the stimulated muscle medium are centrifugation filters; evaporation; and heating.

In some embodiments, centrifugal filters are ultrafiltration filters which can separate small particles and dissolved molecules from fluids based primarily on molecular size, are used to fractionate the muscle stimulated medium to isolate or concentrate for specific cytokines of interest. In some embodiments, the filter/membrane is regenerated cellulose, polyethersulfone (PES) or PVDF. In some embodiments, the ultrafiltration filters have a 3,000 nominal molecular weight limit (NMWL), a 5,000 NMWL, a 7,500 NMWL, a 10,000 NMW, a 15,000 NMWL, a 20,000 NMWL, a 30,000 NMWL, a 35,000 NMWL, a 40,000 NMWL, a 50,000 NMWL, a 60,000 NMWL, a 70,000 NMWL, 80,000 NMWL, a 90,000 NMWL, a 100,000 NMWL, or greater NMWL.

Compositions

In some aspects, provided herein are compositions comprising an amount of stimulated muscle medium and/or myokines isolated therefrom and a pharmaceutical excipient. In some embodiments, the amount of stimulated muscle medium and/or myokines is a therapeutically effective amount.

The composition can comprise a pharmaceutically acceptable excipient, a pharmaceutically acceptable salt, diluents, carriers, vehicles and such other inactive agents well known to the skilled artisan. Vehicles and excipients commonly employed in pharmaceutical preparations include, for example, talc, gum Arabic, lactose, starch, magnesium stearate, cocoa butter, aqueous or non-aqueous solvents, oils, paraffin derivatives, glycols, etc. Solutions can be prepared using water or physiologically compatible organic solvents such as ethanol, 1,2-propylene glycol, polyglycols, dimethylsulfoxide, fatty alcohols, triglycerides, partial esters of glycerine and the like. Parenteral compositions may be prepared using conventional techniques that may include sterile isotonic saline, water, 1,3-butanediol, ethanol, 1,2-propylene glycol, polyglycols mixed with water, Ringer's solution, etc.

Compositions may include a preservative and/or a stabilizer. Non-limiting examples of preservatives include methyl-, ethyl-, propyl-parabens, sodium benzoate, benzoic acid, sorbic acid, potassium sorbate, propionic acid, benzalkonium chloride, benzyl alcohol, thimerosal, phenylmercurate salts, chlorhexidine, phenol, 3-cresol, quaternary ammonium compounds (QACs), chlorbutanol, 2-ethoxyethanol, and imidurea.

In some embodiments, the composition may include a cryoprotectant agent. Non-limiting examples of cryoprotectant agents include a glycol (e.g., ethylene glycol, propylene glycol, and glycerol), dimethyl sulfoxide (DMSO), formamide, sucrose, trehalose, dextrose, and any combinations thereof.

In general, the compositions provided herein can be formulated for administration to a subject by any of the accepted modes of administration. Various formulations and drug delivery systems are available in the art. See, e.g., Gennaro, A. R., ed. (1995) *Remington's Pharmaceutical Sciences*, 18th ed., Mack Publishing Co. In some embodiments, the composition is formulated for intravenous, intraperitoneal, or intratumoral delivery. In other embodiments, the composition is present in a skin patch.

Methods of Treatment

The compositions described herein are useful in treating diseases or disorders, for example, cancer and metabolic diseases such as fatty liver disease (i.e., NAFLD), diabetes, obesity, heart disease, and osteoporosis. In some aspects provided herein are methods of treating or preventing a cancer in a patient in need thereof comprising administering to the patient an effective amount of a composition comprising stimulated muscle medium and/or myokines isolated therefrom.

Cancers or tumors that can be treated by the compositions and methods described herein include, but are not limited to: biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute lymphocytic and myelogenous leukemia; intraepithelial neoplasms, including Bowen's disease and Paget's disease; liver cancer (hepatocarcinoma); lung cancer; lymphomas, including Hodgkin's disease and lymphocytic lymphoma; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer, including adenocarcinoma and Wilms tumor. In some preferred embodiments, the cancer is breast cancer, colorectal cancer, endometrial cancer, hepatocellular carcinoma, non-small cell lung cancer, ovarian cancer, or prostate cancer.

In some embodiments, the cancer is a solid tumor. In some embodiments, the solid tumor is reduced in size.

An effective amount of such compositions can readily be determined by routine experimentation, as can the most effective and convenient route of administration, and the most appropriate formulation. An effective amount or a therapeutically effective amount or dose of a composition refers to the amount of the composition that results in amelioration of symptoms or a prolongation of survival in a subject. Toxicity and therapeutic efficacy of such compositions can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Compositions that exhibit high therapeutic indices are preferred.

In some embodiments, the composition is administered by direct injection or perfusion into the solid tumor. In other embodiments, the composition is administered intravenously, intraperitoneally, or intratumorally.

In some embodiments, the patient a second therapeutic that is different than said stimulated muscle medium and/or myokines isolated therefrom. The therapeutic can be any useful agent and/or procedure for the treatment, remission or attenuation of a disease state, physiological condition, symptoms, or etiological factors, or for the evaluation or diagnosis thereof. A therapeutic agent may be a chemotherapeutic agent, for example, mitotic inhibitors, topoisomerase inhibitors, steroids, anti-tumor antibiotics, antimetabolites, alkylating agents, enzymes, proteasome inhibitors, immunotherapy, any combinations thereof and the like. Therapeutic procedures include radiation, surgery, and the like.

In some embodiments, the second therapeutic is abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, imatinib, hydroxyurea, imatinib, lapatinib, leuprorelin, melphalan, methotrexate, mitoxantrone, nedaplatin, nilotinib, oxaliplatin, paclitaxel, pazopanib, pemetrexed, picoplatin, romidepsin, satraplatin, sorafenib, vemurafenib, sunitinib, teniposide, triplatin, vinblastine, vinorelbine, vincristine, or cyclophosphamide.

In some embodiments, a sub-therapeutic dose of the second therapeutic is administered to the subject. "Sub-therapeutic" means an amount less than that which normally would produce an anxiolytic effect when given to a subject. In some embodiments, the sub-therapeutic amount is one quarter to one half the normal daily dosage.

In some embodiments, the stimulated muscle medium and/or myokines and the second therapeutic are delivered substantially simultaneously, concurrently or sequentially.

Fatty liver disease (FLD, also known as hepatosteatosis) is a prevalent liver condition that occurs when lipids accumulate in liver cells, unrelated to alcohol use, but linked to obesity, diabetes and dyslipidemia. The lipid accumulation causes cellular injury and sensitizes the liver to further injuries. The accumulated lipids may also impair hepatic microvascular circulation. In other aspects provided herein are methods of treating and/or preventing fatty liver in a patient in need thereof comprising administering to the patient an effective amount of stimulated muscle medium and/or myokines.

Monitoring Exercise

In some aspects provided herein are methods for titrating physical activity for the treatment and/or prevention of cancer, which methods comprise: detecting or measuring the level of a myokine in a biological sample isolated from a subject; and reporting the level of the myokine to the subject or providing to the subject instruction to or not to exercise, wherein the instruction is determined from the level of myokine detected or measured. In some embodiments, the subject increases an amount, intensity or a duration of an exercise when the level of myokine is below a pre-determined baseline.

The term "biological sample" refers to a sample obtained from a subject, including sample of biological tissue or fluid origin obtained in vivo or in vitro. Such samples can be, but are not limited to, body fluid (e.g., blood, blood plasma, serum, or urine), organs, tissues, fractions, and cells isolated from mammals including, humans. Biological samples also may include sections of the biological sample including tissues (e.g., sectional portions of an organ or tissue). Biological samples may also include extracts from a biological sample, for example, an antigen from a biological fluid (e.g., blood or urine). In preferred embodiments, the biological sample is blood, tear, saliva, sweat, or urine. In other preferred embodiments, the biological sample is obtained by noninvasive techniques, for example, from tears, saliva, sweat, or urine.

The presence or level of a myokine in the biological sample can be determined using any method known in the art. Non-limiting examples include antibody arrays, spectroscopy, column chromatography; HPLC; FPLC; matrix-affinity chromatography; reverse-phase chromatography; optical spectroscopic techniques; and electrophoretic separation.

Other aspects of the disclosure provide devices for titrating physical activity for the treatment and/or prevention of cancer, which devices comprise: an assembly configured to receive a biological sample; a detector for measuring an amount of myokine in biological sample; and a display for reporting the amount of myokine in the biological sample or an instruction to or not to exercise. In some embodiments, the device is wearable or handheld. In other embodiments, the device is configured to communicate with a wearable or handheld device. The user of the device may be the subject exercising or it may be not be the subject exercising, for example, a healthcare professional. In some embodiments, the device for titrating physical activity reports instruction to exercise or not to exercise in real time. In other embodiments, the device for titrating physical activity reports a prediction of how much more exercise is needed to obtain a pre-determined level of a specific myokine(s).

EXAMPLES

The following examples are intended to further illustrate certain embodiments of the disclosure. The examples are put forth so as to provide one of ordinary skill in the art and are not intended to limit its scope.

Example 1: Anti-Proliferative Effect of Secreted Factor(s) from Skeletal Muscles on Colorectal Cancer and Breast Cancer One largely underexplored epidemiological observation has been the striking (~25%) reduction in colorectal cancer (CRC) attributable to exercise (even after controlling for confounders such as obesity and diabetes) (Robsahm et al., Eur J Cancer Prev. 2013). Interventional trials suggest a reduction in colonic epithelial proliferation (McTiernan et al., CEBP 2006). However, the biological mechanisms remain unclear with most groups focused on increased insulin sensitivity.

Colorectal cancer (CRC) cell lines HT-29, HCT-116 and immortalized mouse myoblast cell line C2C12 were obtained from American Type Culture Collection (ATCC, Manassas, Va.). Colon cancer cell lines were cultured in McCoys 5A modified medium containing 10% FBS and 0.5% penicillin/streptomyocin (p/s). C2C12 cells were cultured in DMEM medium containing 10% FBS and 0.5% pen/strep. C2C12 cells were differentiated into myotubules by supplementing them in low glucose DMEM (1 g/L) containing 2% horse serum and 0.5% p/s (differentiation medium).

C2C12 were then seeded onto 6-well tissue culture plates at a density of 50,000 cells/ml and grown to a confluency of ~80-90%. Once this confluency was obtained cells were rinsed 2× in Dulbecco's Phosphate-Buffered Saline (DPBS) and supplemented with differentiation medium for 7-9 days. Cells were deemed ready for contraction once >80% cell population has differentiated/exhibited myotubule formation and nuclear fission has occurred within network of myotubules. Myotubules were rinsed 2× in DPBS and 2.5 ml of Krebs Ringer Buffer solution was added to each well, a buffer used for conduction. 6-well plates were fitted with 6-well specific electrodes and connected to the C-Pace contraction apparatus (Ionoptix, Milton, Mass., USA). Cells were contracted for 12 hrs at 20 mV for a pulse duration at 3 ms.

Krebs ringer buffer solution used to contract myotubules was collected after contraction treatment. Medium was centrifuged at 800 rpm for 5 minutes at 4 degrees C. to remove any detached cells. Supernatant was collected and placed in Amicon Ultra Centrifugal filters (3 kDa filter) and centrifuged at 4000 rpm for 60 min at 4 degrees C. Concentrate was collected, yielding ~100-200 uL volume. Concentrate was resuspended in McCoy's 5A medium at a ratio of 2:1 original volume of Krebs ringer buffer to McCoys medium. For example, if 12 ml of Krebs ringer buffer was originally obtained concentrated, then the concentrate would be resuspended in 6 ml of McCoys medium.

CRC cell lines HCT-116 and HT-29 were seeded in 6-well plates and grown to a confluency of ~70%. Cells were treated with myotubule contracted concentrate for 48 hrs. Protein was isolated for western blot analysis for assessment of phospho-MEK1/2, PCNA, cyclin D1, and phospho-Rb. Briefly, protein was isolated using 1× cell lysis buffer containing protease and phosphatase inhibitor. Protein was standardized using Bradford Quickstart assay and stabilized in lammeli buffer. Protein was subjected to SDS-PAGE using Criterion Cell/Transfer System with 4-20% Criterion TGX gels and transferred onto 0.2 uM PDVF membranes. Membranes were blocked with 5% non-fat milk blotter and probed for protein markers/primary antibodies overnight. Membranes were washed 1× with TBST and incubated with anti-rabbit secondary antibody for 1 hr. Membranes were developed using UVP Darkroom developer and analyzed for protein densitometry using UVP software.

Figure 2A:
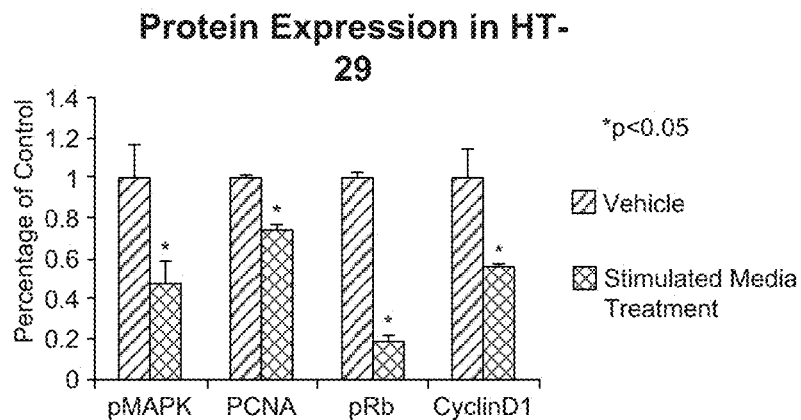
FIG. 2 demonstrates a secreted factor(s) from skeletal muscle reduces expression of proliferative markers and cell cycle regulators pMEK1/2, PCNA, pRb, and cyclin D1 in colorectal cancer cell lines HT-29 (A), beta catenin expression in HT-29 (B) and pMEK1/2, PCNA, pRb, and cyclin D1 HCT-116 (C).
Figure 2B:
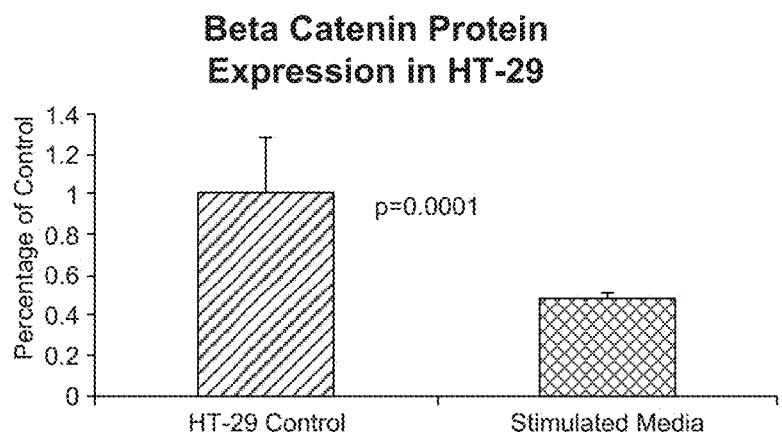
Figure 2C:
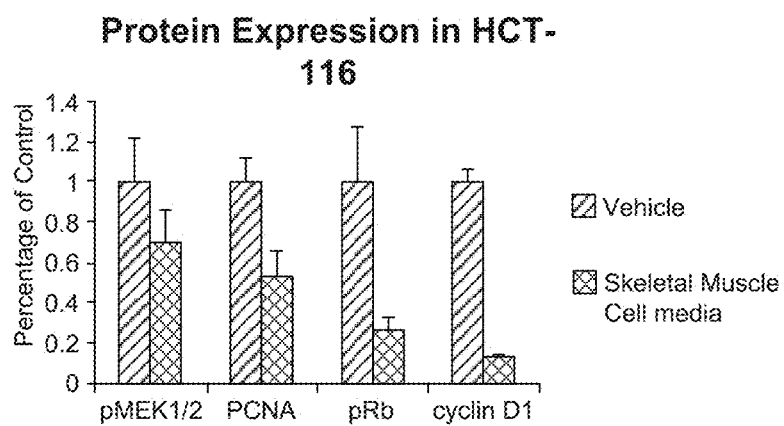

The results indicate that a secreted factor(s) from skeletal muscles likely plays a role in the anti-proliferative effect that is a hallmark of exercise's anti-neoplastic properties. In particular, both HT-29 and HCT-116 cells treated with the muscle stimulated medium (skeletal muscle cell media) exhibited statistically significant decreases in pMEK1/2, PCNA, pRB and cyclin D1. FIGS. 2A and 2C. Muscle stimulated medium also showed an approximately 52% reduction in beta catenin protein levels. FIG. 2B. It is contemplated that identification of specific factor(s) secreted from skeletal muscle could, in part, identify molecular targets that could be mimicked by pharmacological agents.

Figure 3A:
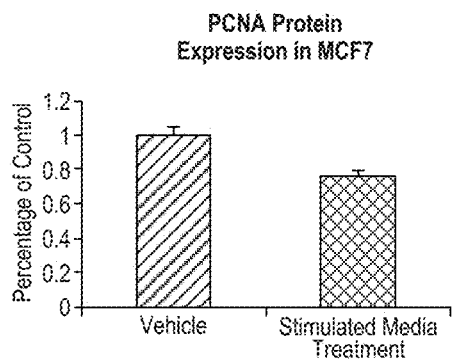
FIG. 3 shows a secreted factor(s) from skeletal muscle also reduce expression of proliferative markers and cell cycle regulators PCNA (A), pRb (B), and p21 (C) in MCF7 breast cancer cells and phosphorylated cyclin D1 (D) and PCNA (E) in the triple negative breast cancer cell line MB468. In addition, MCF7 cells showed an increase in expression of p21, a cyclin-dependent kinase inhibitor (CDK) that can mediate growth arrest and cellular senescence.
Figure 3D:
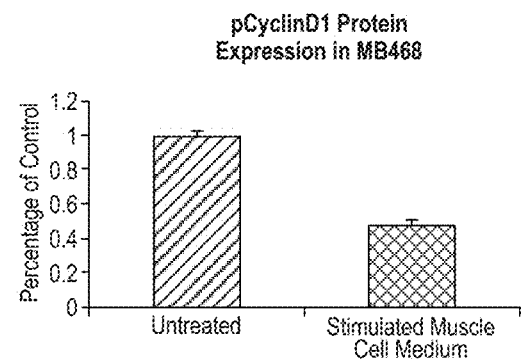
Figure 3B:
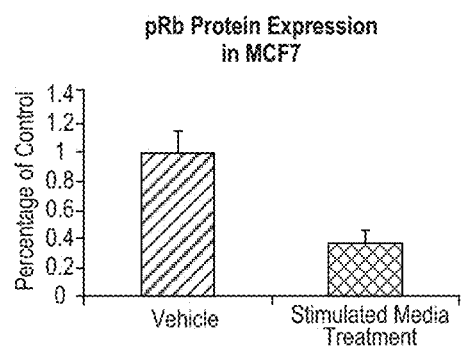
Figure 3E:
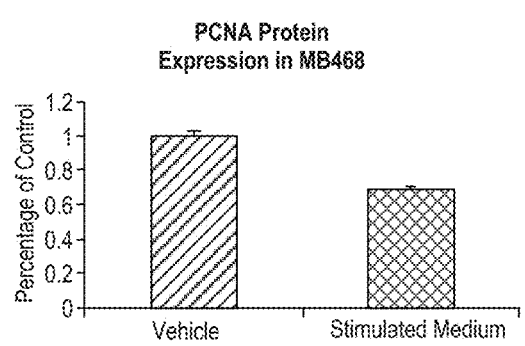
Figure 3C:
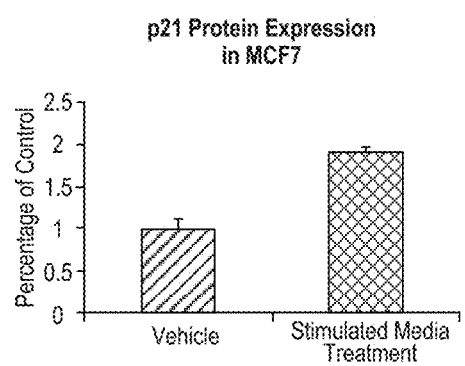

Similar results were observed in breast cancer cell lines (MCF7 and MB468) when treated with muscle stimulated medium. In particular, the proliferative markers and cell cycle regulators PCNA (FIG. 3A), pRb (FIG. 3B) in MCF7 breast cancer cells and phosphorylated cyclin D1 (FIG. 3D) and PCNA (FIG. 3E) in the triple negative breast cancer cell line MB468 were reduced as compared to untreated controls. In addition, MCF7 cells showed an increase in expression of p21 (FIG. 3C), a cyclin-dependent kinase inhibitor (CDK) that can mediate growth arrest and cellular senescence. These data demonstrate an anti-neoplastic effect on CRC cell lines HCT-116 and HT-29 as well as breast cancer cell line MCF-7.

Example 2: Synergistic Effect of Exercise Medium and Chemotherapy Drug

Advances in therapeutics have improved mortality in early and advanced stage CRC, however five-year recurrence remain at 30-50% (O'Connell et al. *J Clin Oncol* 2008). Therefore, identifying factors that can contribute to better outcomes are needed.

To explore the potential synergistic effects of the chemotherapeutic agent 5-fluorouracil (5'FU) HT-29s were seeded in a 96-well plate to determine dosage of 5-flurouracil (5'FU) treatment. Treatment with 25 uM of 5'FU showed the best effect after 48 hrs without suggestion of cytotoxicity due to concentration. HT-29s were plated in 6-well plates and grown to 70% confluency. Cells were treated with either concentrated stimulated muscle media (collected as described above in Example 1), 5'FU or a combination of both for 48 hrs. HT-29 cells subjected to treatments described above were analyzed by western blot analysis for expression of PARP (Poly (ADP-Ribose) Polymerase) expression. PARP are enzymes involved in DNA-damage repair. Inhibition of PARP is a promising strategy for targeting cancers with defective DNA-damage repair.

Figure 4A:
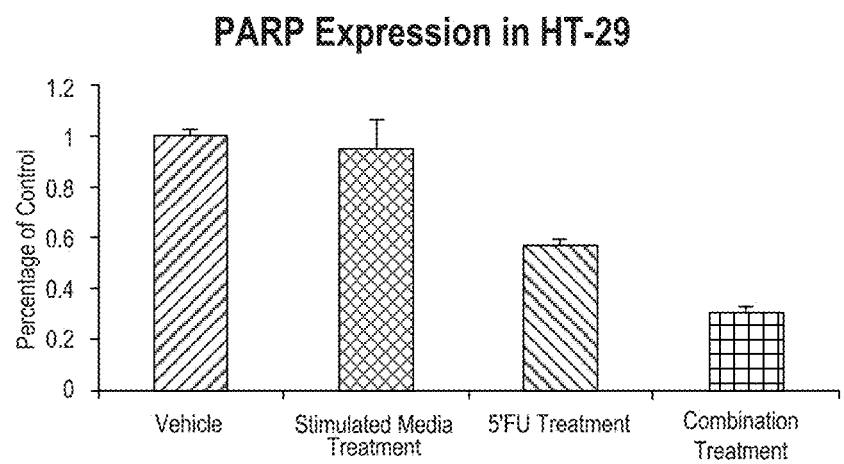
FIG. 4 depicts the synergistic effects of stimulated muscle media and the chemotherapeutic 5-fluorouracil (5'FU) in HT-29 (A) and MB468 (B) cell lines.
Figure 4B:
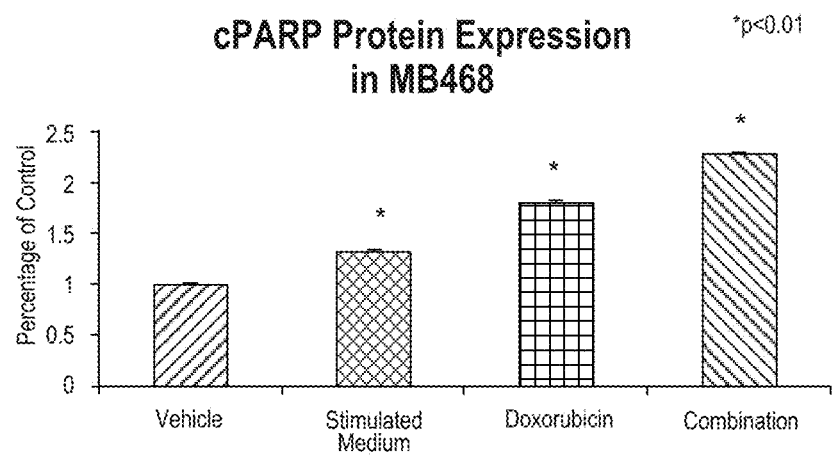

When cells were treated with stimulated muscle media only, there was no significant reduction in PARP expression. Surprising, when cells were treated with a combination of stimulated muscle media and 5'FU there was a significant decrease in PARP expression as compared to controls. In addition, the percentage of cells expressing PARP was even lower in the cells treated with the combination as compared to 5'FU treatment. FIG. 4.

Example 3: Myokines Secreted from Exercising Skeletal Muscle Cells Affect the Metabolic Profile of Hepatocellular Carcinoma (HCC) Cells Muscle stimulated medium was prepared similar to as described above. Briefly, C2C12 myoblasts (from ATCC) were cultured in high-glucose DMEM supplemented with 10% fetal bovine serum and 1% penicillin-streptomycin (from Invitrogen) at 37° C./5% $CO_2$. For differentiation, C2C12 myoblasts were seeded into multiple 6 well plates and media was changed to differentiation media (high-glucose DMEM+2% fetal calf serum+1% non-essential amino acids+1% penicillin-streptomycin at about 90-100% confluency. The differentiation media was changed every 24-48 hrs and differentiated myotubules were subjected to electrical pulse stimulation (FPS) after at least 5 days of differentiation.

The medium was changed to 1.5 mL of fresh Krebs-Ringer buffer (KRB) per well (6 well plates) immediately before the contraction study. The 6-well plates were connected to the electrical stimulation apparatus and stimulated by electric pulses generated by an electrical pulse generator (Uchida Denshi, Hachioji, Japan). Differentiated C2C12 myotubules were stimulated with electric pulses of 50 V at 1 Hz for 3 ms at 997-ms intervals for 9 hrs under standard growth environment. The control set consisted of equal number of 6-wells plates with parallel media changes and KRB during last 9 hrs. Contraction of myotubules was visualized and documented (data not shown). In some experiments, differentiated C2C12 myotubules were stimulated 20V 1 Hz 3 milisecond shocking gave the most desirable results in terms of amount of myokines collected without disturbing the viability of myotubules. Of note, over a prolonged period of time, myotubules develop "fatigue" which leads to time-dependent decrease in the rate of myokine production, and it was found that shocking for ~9 hrs was an optimal and convenient duration.

Medium was collected from shocked and unshocked C2C12 cells was collected separately in 50 mml tubes and centrifuged at 1000 rpm for 10 minutes, to make sure there was no residual debris from myotubules. To concentrate myokines (molecular weight between 5-20 KD), the debris-free KRB was transferred to 3K-Amicon tubes (Merck) and centrifuged at 4000 rpm for 70-75 minutes. Supernatant (typically 200 microliters from total 15 ml of collected KRB) would presumably have higher concentration of myokines in the subset obtained from shocked C2C12 myotubule s.

Figure 5A:
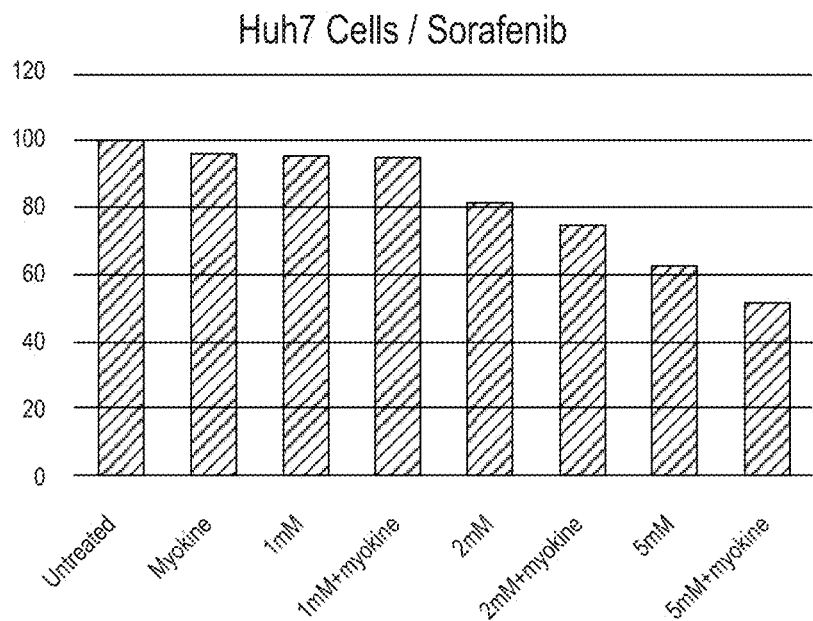
FIG. 5 shows decrease in cellular proliferation of Huh7 (A) and HepG2 (B) hepatocellular carcinoma (HCC) cells when treated with the chemotherapeutic sorafenib and the synergistic effects of stimulated muscle media and sorafenib.
Figure 5B:
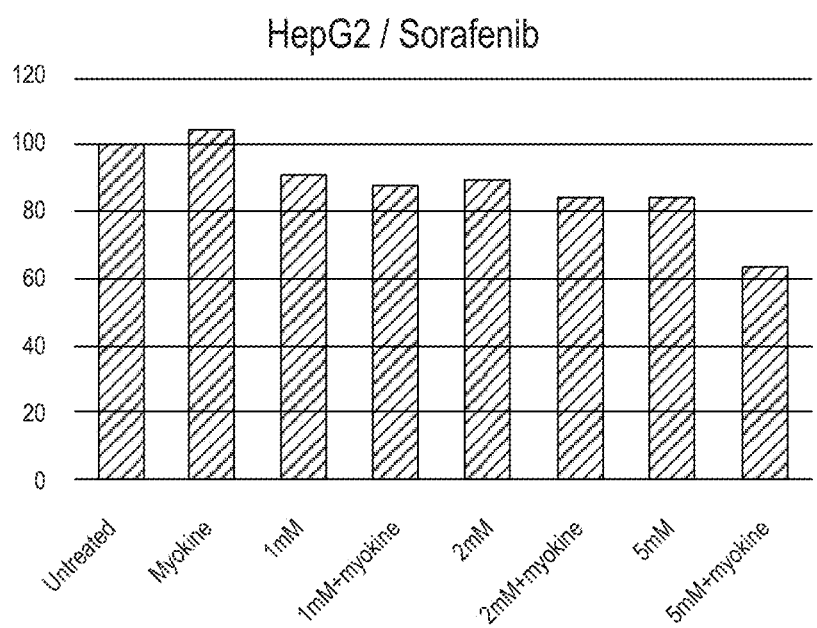

Two HCC cell lines-HepG2 and HuH7. Cells were seeded into 6-well plates and treated with concentrated KRB from shocked C2C12 myotubes (+myokine group) and unshocked C2C12 myotubes (-myokine group) for 24-48 hrs with or without Sorafenib (at 1 micromolar, 2 micromolar and 5 micromolar concentrations) with suitable parallel control treatments (DMSO). For WST assay, similar treatments were carried out in 96-well plates. A decrease in cellular proliferation of Huh7 (FIG. 5A) and HepG2 (FIG. 5B) hepatocellular carcinoma (HCC) cells was observed when treated with the chemotherapeutic sorafenib and the synergistic effects of stimulated muscle media and sorafenib.

Cell lysates were separated by sodium dodecyl sulfate-polyacrylamide gel electrophoresis and transferred to polyvinylidene fluoride membranes. The membranes were blocked with Tris buffered saline comprising 2.5% non-fat dry milk, 2.5% bovine serum albumin, and 0.1% Tween 20. Membranes were incubated overnight with appropriate primary antibodies (Cell Signaling Technology, Boston, Mass., USA), and secondary antibody conjugated to horseradish peroxidase (Santa Cruz Biotechnology, Dallas, Tex., USA) was used for detection by enhanced chemiluminescence.

Figure 6A:
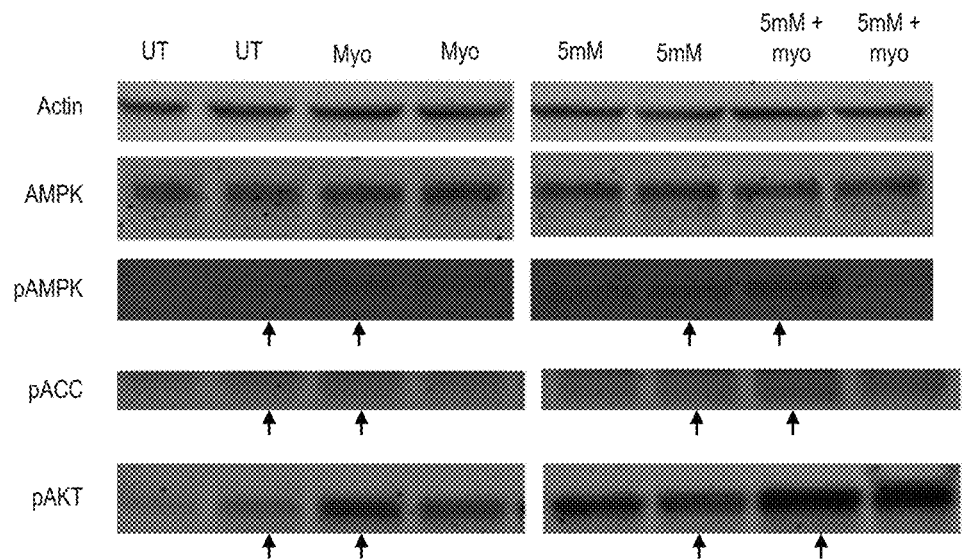
FIG. 6A depicts metabolic changes observed in HepG2 cells when treated with stimulated muscle media alone (Myo), sorafenib (5 mM) and the synergistic effects of stimulated muscle media and sorafenib (5 mM+myo).
Figure 6B:
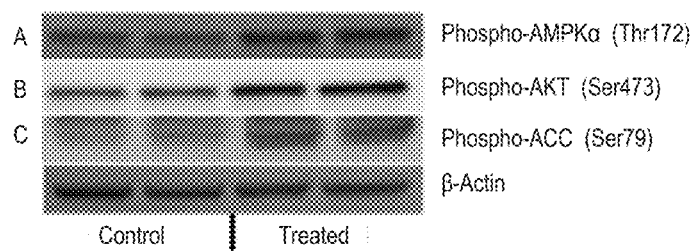
FIG. 6B demonstrates that treatment of HepG2 cells stimulated muscle media lead to increased levels of pAMPKα (A: 90%, $p<0.05$), pAKT (B: 150%, $p<0.05$), pACC (C: 75%, $p<0.05$) compared to control.
Figure 6C:
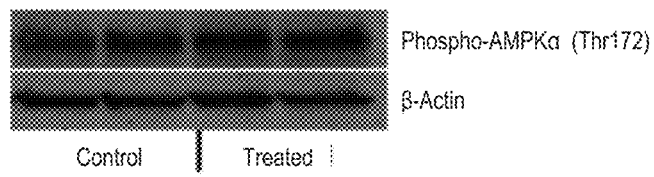
FIG. 6C demonstrates that fragmentation of the stimulated muscle media can alter the observed effect on pAMPKα expression levels.
Figure 7A:
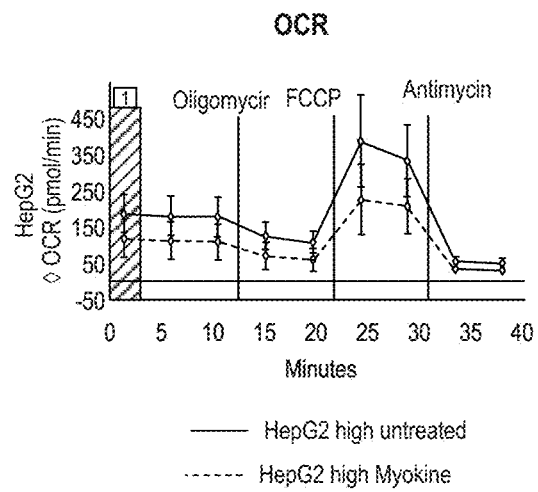
FIG. 7 demonstrates real time shifts in metabolic pathways observed in HepG2 and Huh-7 cells treated with myokines. A decrease in extracellular acidification rate (ECAR) was observed, indicating a reduced glycolysis rate for both HepG2 (B) and Huh-7 (D) cell lines. A non-significant decrease in oxygen consumption rate (OCR) was observed for both HepG2 (A) and Huh-7 (C) cell lines.
Figure 7B:
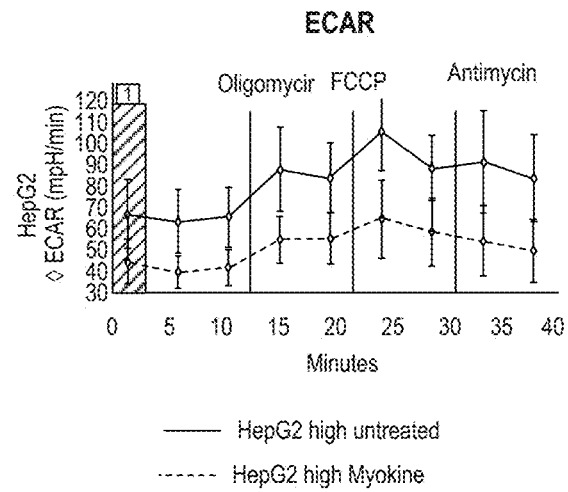
Figure 7C:
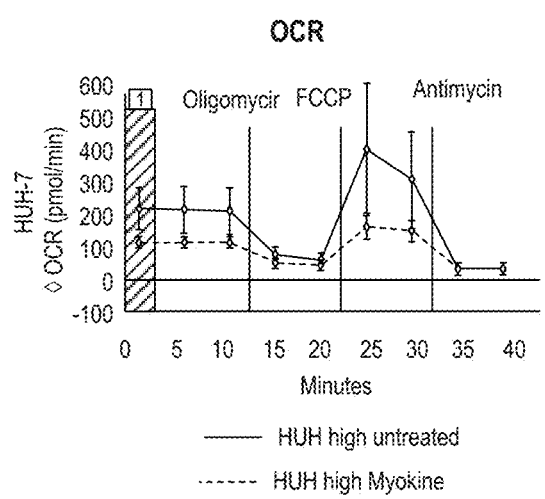
Figure 7D:
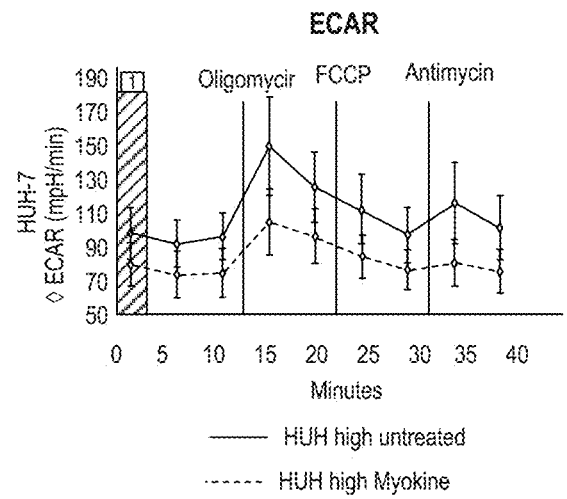
Figure 8A:
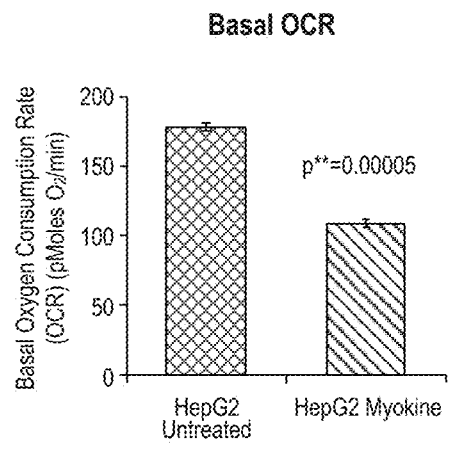
FIG. 8 demonstrates that HepG2 cells exhibit a decrease in basal OCR (A) following treatment with myokines without a significant change in ATP synthesis (B). In addition, HepG2 cells exhibited a significant decrease in proton leakage (C) and ECAR (D).
Figure 8B:
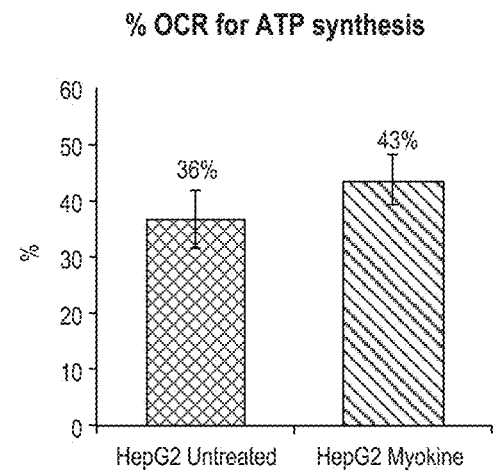
Figure 8C:
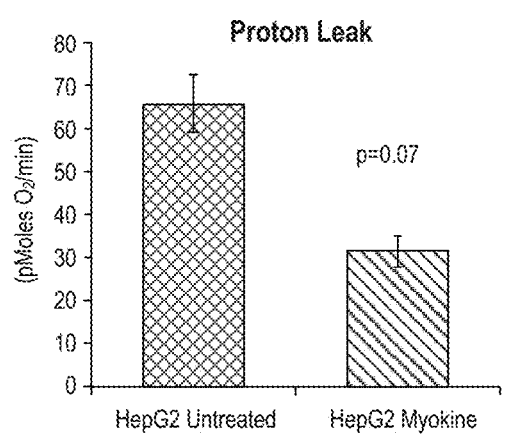
Figure 8D:
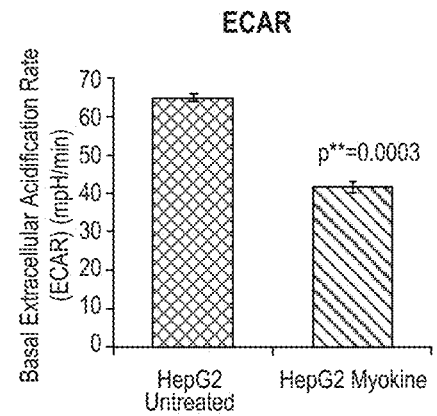
Figure 9A:
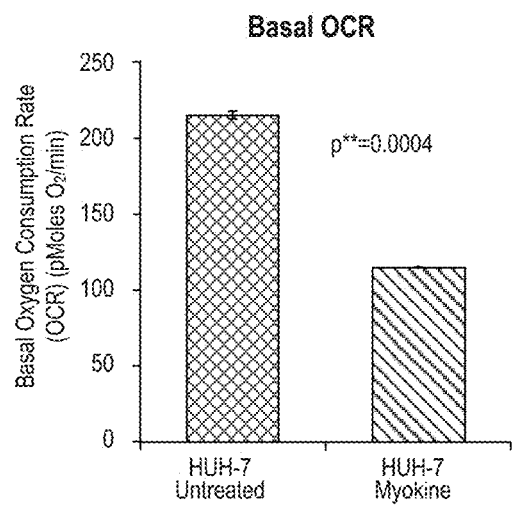
FIG. 9 demonstrates that Huh-7 cells exhibit a decrease in basal OCR (A) following treatment with myokines without a significant change in ATP synthesis (B). HepG2 cells also exhibited a significant decrease in ECAR (C). Global Lipidomic analysis of HepG2 cells treated with exercise-conditioned media demonstrated a significant decrease in total free fatty acid level (28% decrease; $p<0.05$) (D).
Figure 9B:
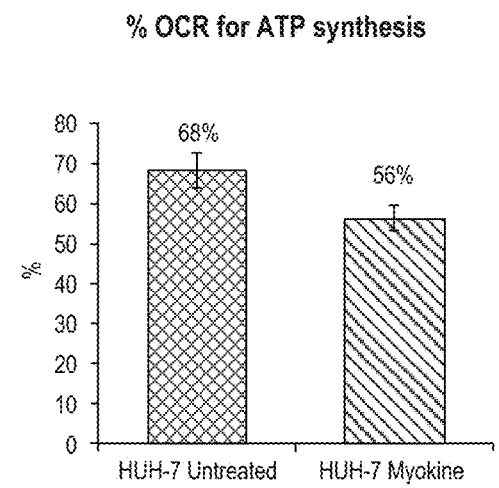
Figure 9C:
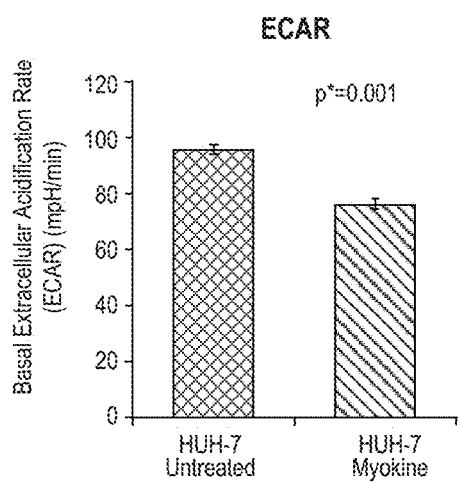
Figure 9D:
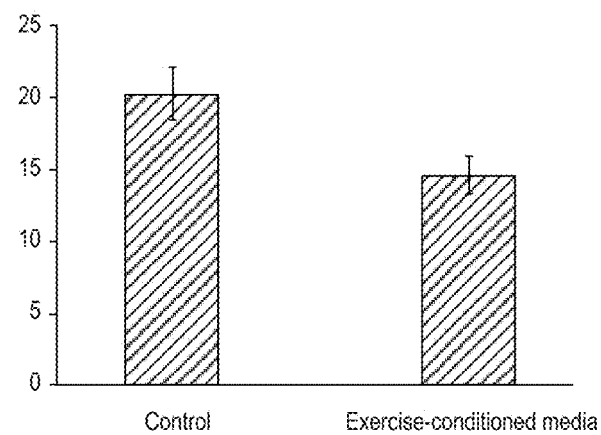

As shown in FIG. 6, metabolic changes were observed in HepG2 cells when treated with stimulated muscle media alone (Myo), sorafenib (5 mM) and the synergistic effects of stimulated muscle media and sorafenib (5 mM+myo). For example, an increase in pAMPK (activated AMP-activated protein kinase) expression was observed after myokine treatment and sorafenib treatment alone. These effects were further augmented by the combination of stimulated muscle media and sorafenib, with similar results also being observed for pACC and pAKT. Exercise is known to activate AMP-activated protein kinase in skeletal muscles. When activated, AMPK stimulates energy generating processes such as glucose uptake and fatty acid oxidation and decrease energy consuming processes such as protein and lipid synthesis, thus improving the metabolic status. In particular, for cancer cells, AMPK is considered to be a metabolic tumor suppressor. These data suggest that a secreted factor(s) present in the muscle stimulated media collected in vitro can induce similar beneficial effects on other cells, such as acting, at least in part, as tumor suppressors for cancer prevention and therapy.

In addition, experiments using Seahorse XF Analyzers (Seahorse Biosciences, North Billerica, Mass., USA) were performed to measure oxygen consumption rate (OCR) and extracellular acidification rate (ECAR) in real-time. OCR is an indicator of mitochondrial respiration and ECAR is a marker of lactate production and glycolysis. In these experiments with two HCC cell lines-HepG2 and Huh7, it was observed that treatment with myokines resulted in profound decrease in ECAR in both cells lines, indicating reduced glycolysis rate. FIG. 7. Interestingly, although there was a decrease in basal OCR post myokine treatment, the percentage of OCR for ATP synthesis did not change significantly, indicating a preference towards mitochondrial respiration as the major source of energy production in cells treated with myokines. FIGS. 8 and 9. When the exercise-conditioned media was centrifuged to selectively isolate molecules above molecular weight 50 kiloD, the observed effect with pAMPKα was lost (*D), indicating that mediator molecules are within the range 3-50 kD (molecular weight range for myokines). This supports a role of exercise media, in particular certain fractions of exercise-conditioned media, in both anti-metabolic and anti-carcinogenic processes and for use in the treatment and/or prevention of diseases such as NAFLD-NASH and cancer.

Example 4: Analysis of Myokines Secreted from Fresh and Frozen Samples

Figure 10:
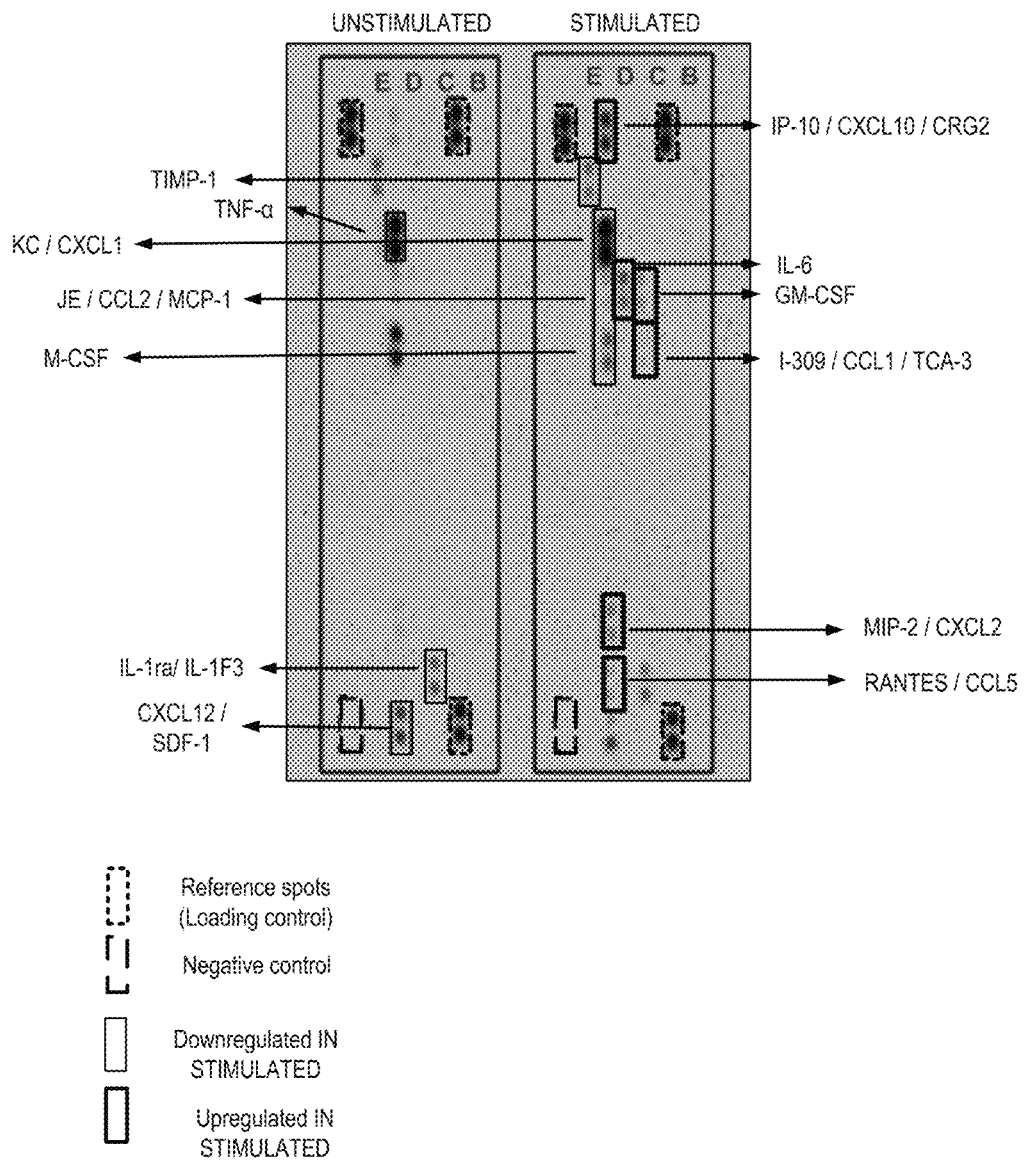
FIG. 10 shows cytokines detected in fresh unstimulated and stimulated mouse muscle media.

To determine which cytokines (i.e., myokines) are released by contracted C2C12 myotubules, a mouse cytokine array panel was performed. Briefly, C2C12s were electrically stimulated for 8 hrs in Krebs Ringer buffer solution (KRB). KRB from unstimulated and stimulated C2C12s were concentrated with Amicon filter tubes (3 kDa filter size) (EMD Millipore). Cytokine array panels (nitrocellulose panel) were then incubated in either fresh (i.e., unfrozen) unstimulated or fresh stimulated KRB for approximately 24 hrs. Panels were developed to reveal cytokines present in KRB. FIG. 10 shows cytokines present, with boxes denoting change in release/presence in cytokines.

Figure 11:
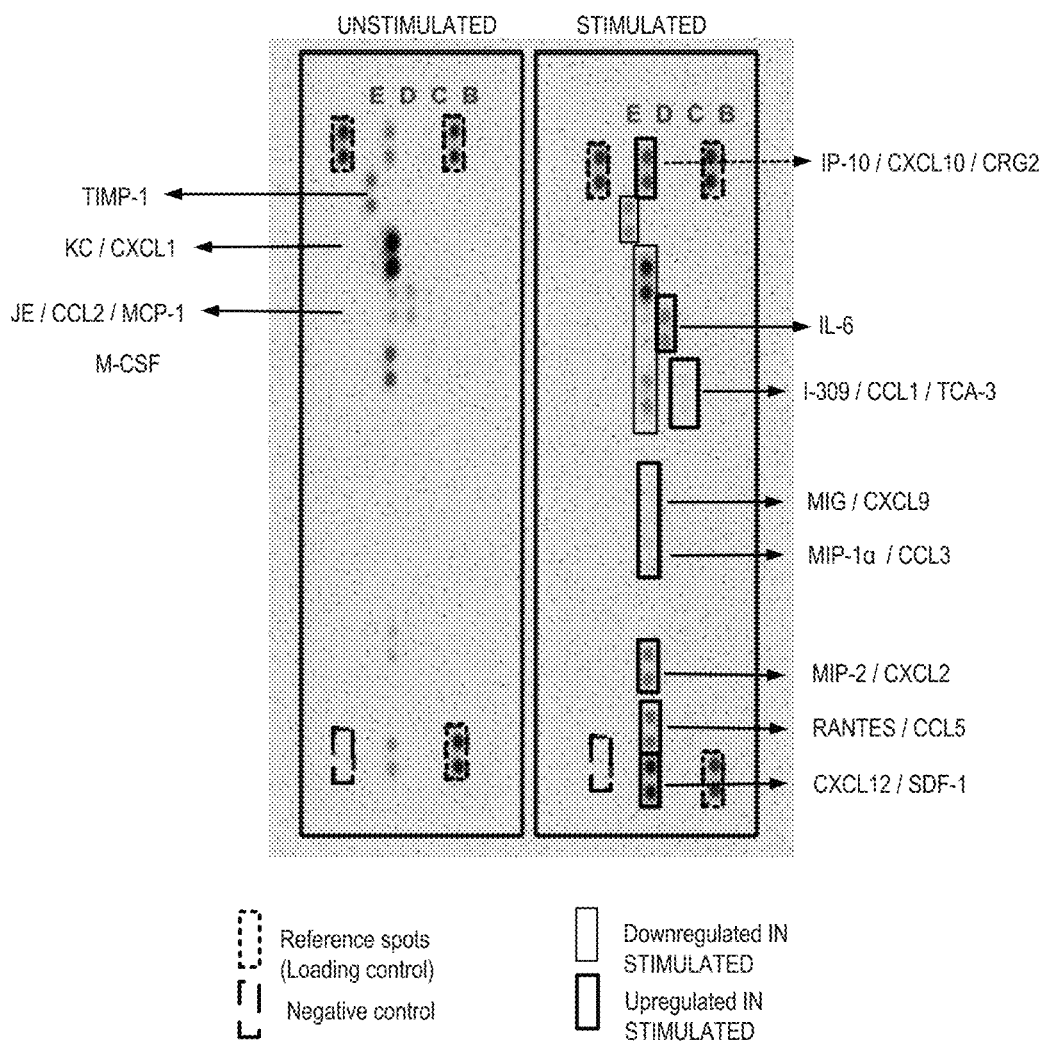
FIG. 11 shows cytokines detected in frozen unstimulated and stimulated mouse muscle media.

To determine if KRB solution can be frozen, for example, at −80° C. for later use, the mouse cytokine array experiment described above was performed on frozen samples. FIG. 11 shows the presence of the same cytokines as detected in the fresh sample as shown in FIG. 10. CXCL-10 and CCL-5 represent two cytokines of particular interest. CXCL10 is a member of the CXC chemokine family which binds to the CXCR3 receptor to exert its biological effects. CXCL10 is involved in chemotaxis, induction of apoptosis, regulation of cell growth and mediation of angiostatic effects. It may also play an important role in pathogenesis of cancer1. Emerging reports have also suggested oncogenic functions of CXCL10 driving metastasis. The exact functions of CCL5/RANTES in tumor biology are not well understood. CCL5 production is relevant to inducing anti-tumor immune responses. In contrast, CCL5 is associated with cancer progression and metastasis. CCL5/CCR5 interactions may also favor tumor development. IL-6 is a marker for contraction that is released by contracted cells. Importantly, this data suggests that the stimulated muscle extract can be frozen following collection until required for use and that at least a portion of the cytokines are not degraded following storage. A mouse myokine myoplex assay (Luminex Assay) of 5 candidate markers was then performed to assay level of cytokines present in a sample after 8 hour stimulation or control (unstimulated). As shown in FIG. 12, IL-6 was detected at a higher level in stimulated samples as compared to unstimulated samples. CCL1/TCA-3 was shown to be upregulated in stimulated samples. Reports have associated CCL1 with control of tumor cell entry into the lymph node. Surprisingly, CXCL9 was mildly upregulated in stimulated media. Several reports have suggested a pro-tumorigenic effect of CXCL9.

Figure 13:
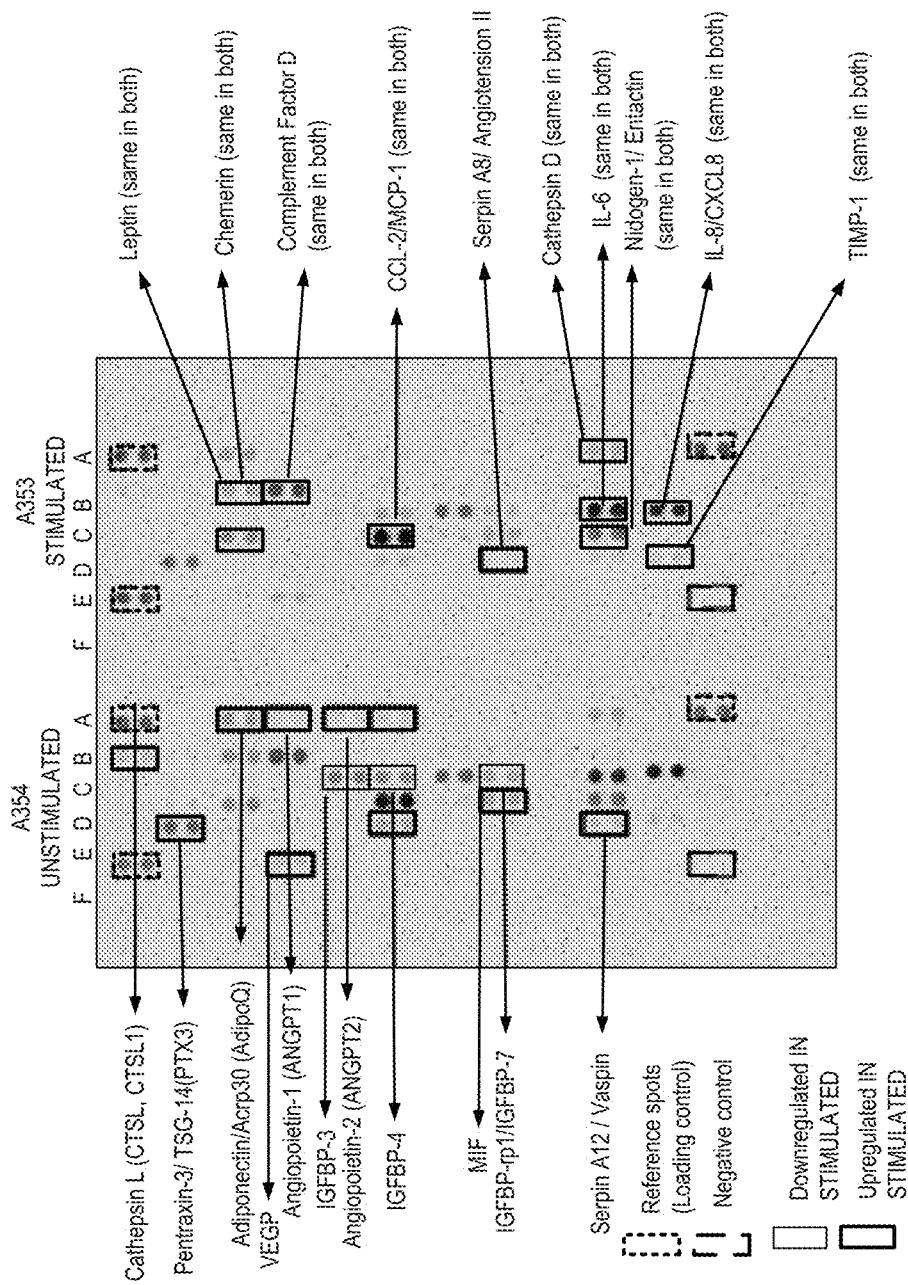
FIG. 13 shows human adipokines detected following treatment of adipocytes with unstimulated and stimulated mouse muscle media.
Figure 14:
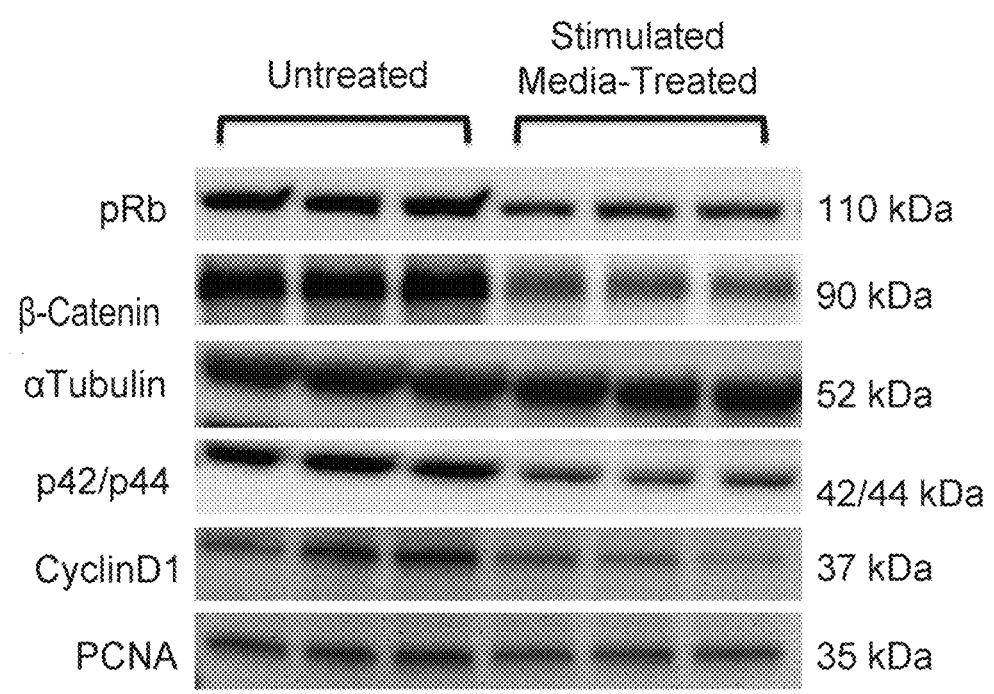
FIG. 14 shows expression levels of cell cycle markers altered in HT29 CRC cells treated with unstimulated or stimulated muscle media.
Figure 15:
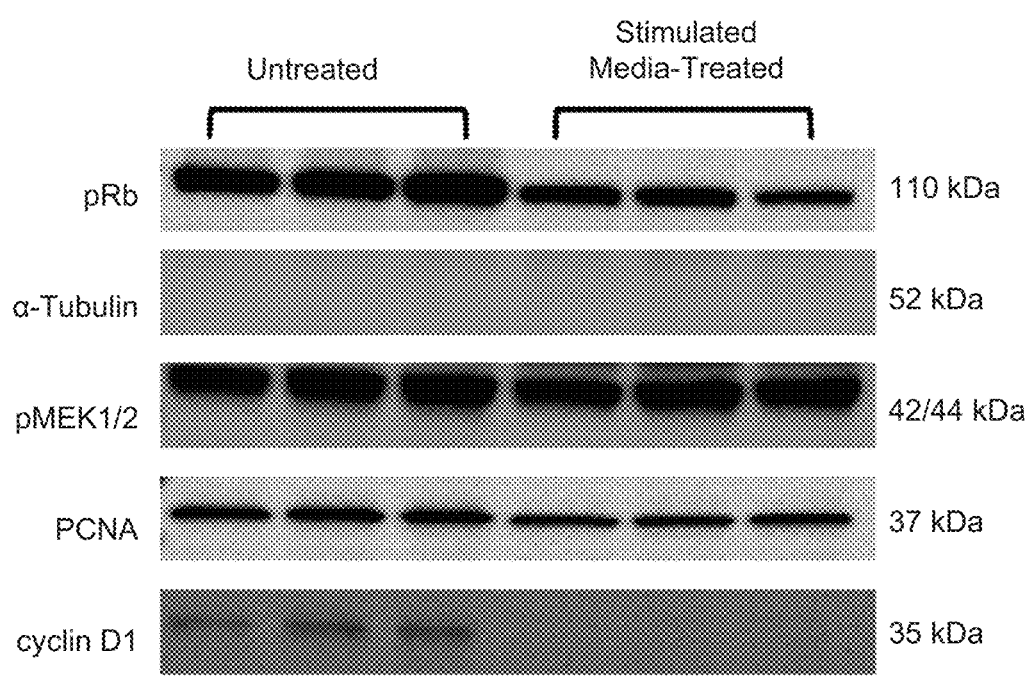
FIG. 15 shows expression levels of cell cycle markers altered in HCT-116 CRC cells treated with unstimulated or stimulated muscle media.
Figure 16:
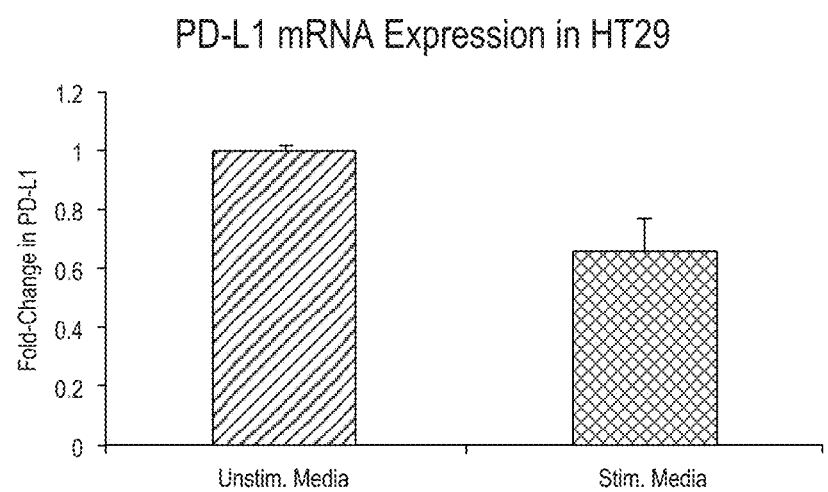
FIG. 16 shows reduced expression levels of PDL1 in HT29 CRC cells treated with unstimulated or stimulated muscle media.
Figure 17:
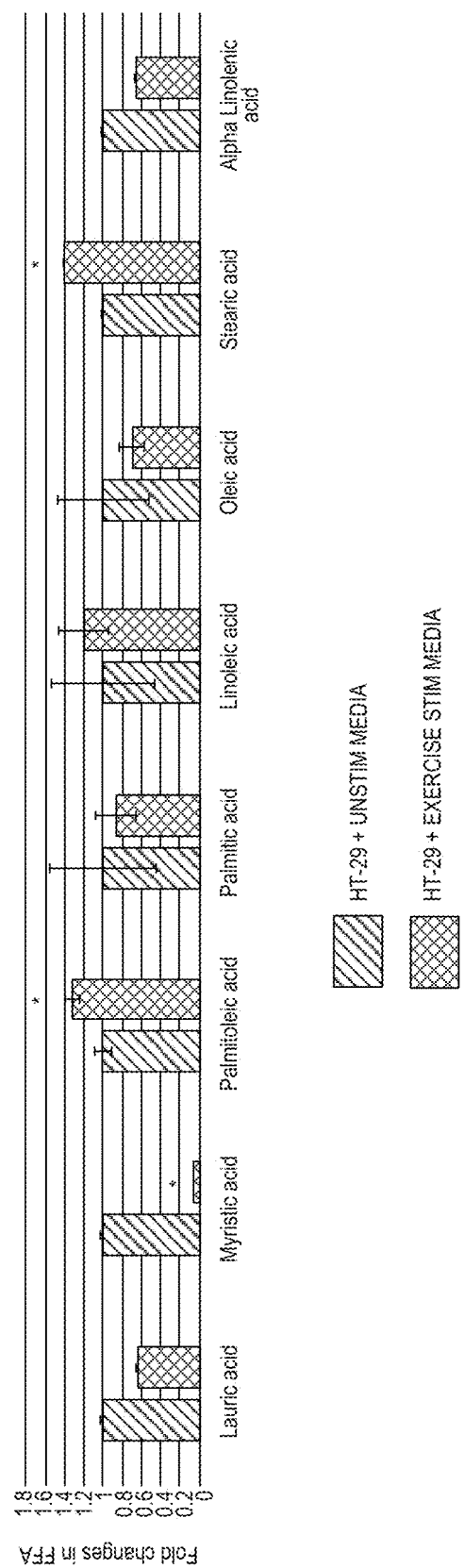
FIG. 17 shows changes in expression of free fatty acids in HT29 CRC cells treated with unstimulated or stimulated muscle media.
Figure 18A:
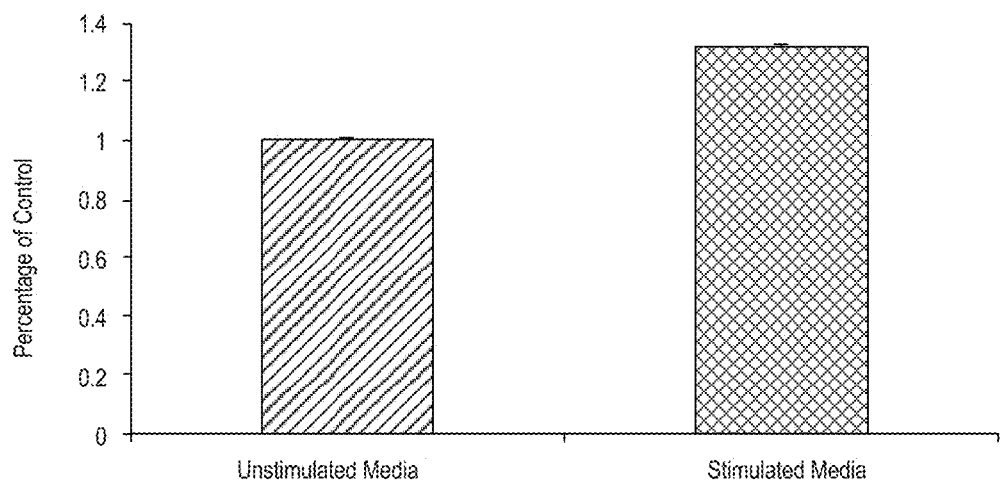
FIG. 18 shows changes in expression of pSERBP1c in HT29 CRC cells (A) and FASN in HT29 and HCT 116 CRC cells treated with unstimulated or stimulated muscle media.
Figure 18B:
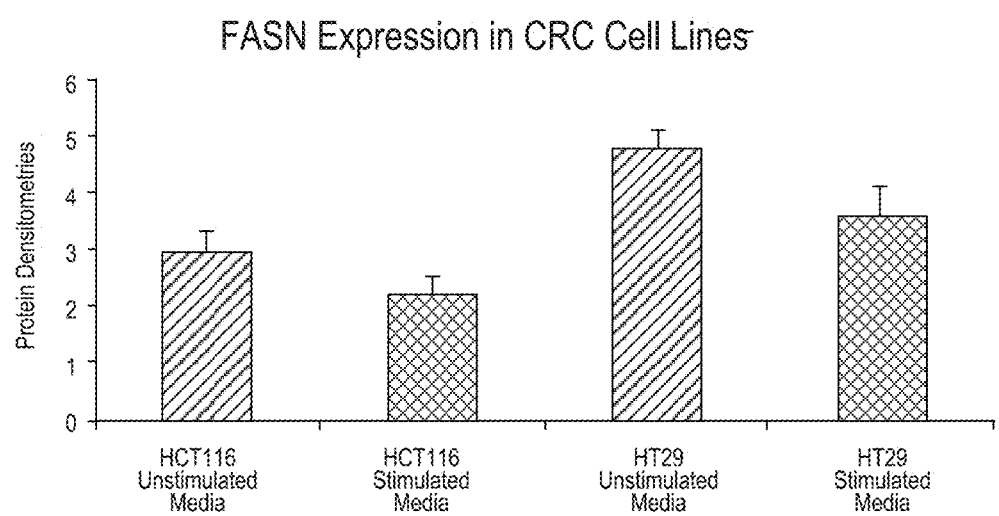

In order to evaluate the ability of exercise-induced myokines to potentiate their effect through modulation of adipokines, primary human adipocytes were treated with myokines for several days. Striking alterations in levels of several adipokines implicated in cell growth and inflammation were noted. FIG. 13. This provides a modality through which adipokines, which have been implicated in neoplastic (e.g. colon cancer, breast cancer) and metabolic processes (e.g. diabetes and NAFLD). Interestingly, Cathepsin L (CTSL) was downregulated in the samples collected from cells treated with stimulated muscle media as compared to samples collected from cells treated with unstimulated muscle media. CTSL upregulation is a common occurrence in a variety of human cancers. It has also been widely correlated with metastatic aggressiveness and poor patient prognosis. In addition, CTSL has been implicated to contribute to cancer-associated osteolysis, a debilitating morbidity affecting both life expectancy and the quality of life. IGFBP-3 and IGFBP-4 were both upregulated in the stimulated muscle media samples. IGFBP-3 has been reported to have strong anti-tumorigenic and anti-metastatic effects, while IGFBP-4 has been reported to inhibit tumor and colony formation in prostate and colon cancer. Together these data suggest that exercise media (i.e., stimulated media), in particular certain fractions of media, could be useful, at least in part, in the treatment and/or prevention of metabolic diseases (e.g., NAFLD-NASH) and cancer by stimulating secretion of certain adipokines.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains. Accordingly, the invention is not limited except as by the appended claims.

In addition, where the features or aspects of the invention are described in terms of Markush groups, those skilled in the art will recognize that the invention is also thereby described in terms of any individual member or subgroup members of the Markush group.

All publications, patent applications, patents and other references mentioned herein are expressly incorporated by reference in their entirety, to the same extent as if each were incorporated by reference individually. In case of conflict, the present specification, including definitions, will control.

What is claimed:

1. A method of treating a breast cancer and/or a colon cancer in a patient in need thereof comprising administering to the patient an effective amount of a composition comprising stimulated muscle medium prepared from myotubes that have been contracted for about 6 hours to about 12 hours at about 20 millivolts (mV) using a pulse duration of about 3 milliseconds (ms).

2. The method of claim 1, wherein the colon cancer is colorectal cancer.

3. The method of claim 1, wherein the treating results in slowed progression and/or amelioration of the breast cancer and/or the colon cancer as compared to a patient or population of patients treated with a placebo or another agent that is not stimulated muscle medium.

4. The method of claim 1, wherein the composition is administered intravenously, intraperitoneally, intratumorally, subcutaneously, or orally.

5. The method of claim 1, further comprising administering to the patient a second therapeutic that is different than said stimulated muscle medium.

6. The method of claim 5, wherein the second therapeutic is oxaliplatin.

7. The method of claim 6, wherein a sub-therapeutic dose of the second therapeutic is administered.

8. The method of claim 6, wherein the stimulated muscle medium and the second therapeutic are delivered substantially simultaneously, concurrently or sequentially.

9. The method of claim 1, wherein the stimulated muscle medium comprises PCNA, TNF-α, IL-6, IP-10/CXCL10/CRG2, RANTES/CCL5, GM-CSF, I-309/CCL1/TCA-3, Serpin A8/Angiotensin II, or any combination thereof.

10. The method of claim 1, wherein the stimulated muscle medium comprise no or substantially no nidogen-1, cathepsin L (CTSL, CTSL1), pentraxin-3/TSG-14 (PTX3), adiponectin/Acrp30 (ADIPOQ), vascular endothelial growth factor (VEGF), angiopoietin-1 (ANGPT1), IGFBP-3, IGFBP-4, MIF, IGFBP-rp1/IGFBP-7, Serpin A12/Vaspin, TIMP-1, KC/CXCL1, JE/CCL2/MCP-1, M-CSF, or any combination thereof.

11. The method of claim 1, wherein the stimulated muscle medium comprises PCNA and no or substantially no nidogen-1.

12. The method of claim 1, wherein the composition comprises myokines 10 kDa or greater and/or none of the myokines in the composition are less than 10 kDa.

13. A method of modulating a level of one or more proteins in colon cancer cells and/or in breast cancer cells by providing a stimulated muscle medium as in claim 1 that comprises PCNA, TNF-α, IL-6, IP-10/CXCL10/CRG2, RANTES/CCL5, GM-CSF, I-309/CCL1/TCA-3, and/or Serpin A8/Angiotensin II, and comprises substantially no nidogen-1, cathepsin L (CTSL, CTSL1), pentraxin-3/TSG-14 (PTX3), adiponectin/Acrp30 (ADIPOQ), vascular endothelial growth factor (VEGF), angiopoietin-1 (ANGPT1), IGFBP-3, IGFBP-4, MIF, IGFBP-rp1/IGFBP-7, Serpin A12/Vaspin, TIMP-1, KC/CXCL1, JE/CCL2/MCP-1, and/or M-CSF, wherein the proteins are selected from the group of proteins consisting of phosphor-MEK 1/2, PCNA, cyclin D1, phosphor-Rb, β-catenin, and p21.

* * * * *